United States Patent [19]

Emanuel-King

[11] Patent Number: 5,248,503

[45] Date of Patent: Sep. 28, 1993

[54] HERBAL DIETARY SUPPLEMENT

[76] Inventor: Rosalba Emanuel-King, 630 First Ave. (22M), New York, N.Y. 10016

[21] Appl. No.: 816,661

[22] Filed: Jan. 3, 1992

[51] Int. Cl.$^5$ .............................................. A61K 35/78
[52] U.S. Cl. .................................. 424/195.1; 426/590; 426/655
[58] Field of Search ..................... 424/195.1; 426/655, 426/590

[56] References Cited

U.S. PATENT DOCUMENTS 4,506,044  3/1985  Cox et al. ............................... 524/27

*Primary Examiner*—John W. Rollins
*Attorney, Agent, or Firm*—Charles E. Baxley

[57] ABSTRACT

Dietary supplements containing in solution at least two herbal ingredients selected from a group consisting of: mullen leaf, witch hazel, baptisia (wild indigo), marshmallow root (*Althea officianales*), *Potentilla tormentilla*, myrrh, agrimony, blood root (sanguinaria), bistort, echinacea, parsley, eucalyptus, wintergreen, rosemary, ginger, sandalwood, sweet almond, sassafrass, linseed and castor. When ingested transcutaneously the product is holistically effective for reduction of plaque and for treating symptons of gingivitis, gum disorders, cold sores, oral boils, herpes simplex, pimples and acne vulgaris. The holistic product is carried in a treatment medium which may be a liquid solution, drops, gum drops, lozenges, chewing gum, breath dots, toothpaste, a skin patch, an oral rinse, a cream, a poultice, a suppository, a vapor, an inhalter and/or a douche.

2 Claims, No Drawings

HERBAL DIETARY SUPPLEMENT

BACKGROUND OF INVENTION

The Inventor has experimented for years with combinations of herbs for use as dietary supplements. She has discovered such combinations, as claimed herein, with herbs contributing therapeutically to vigorous well being of humans.

FIELD OF INVENTION

This invention relates to herbal dietary supplements as well as to herbal holistic therapeutic products for human ingestion via gums, skin and other cutaneous membranes. More particularly the holistic aspects of this invention deal therapeutically with plaque, gingivitis, gum disorders, cold sores, oral boils, herpes simplex, pimples, acne vulgaris and other disorders susceptible to transcutaneous treatment. As foods, the dietary supplements of this invention are of course eaten. As a holistic therapeutically effective product, the active ingredients are carried in a treatment medium such as a liquid solution, drops, gumdrops, lozenges, chewing gum, breath dots, toothpaste, a skin patch, an oral rinse, a cream, a poultice, a suppository, an inhaler and/or a douche.

SUMMARY OF INVENTION

Applicant teaches a food product, preferably in liquid form, containing in solution two or more ingredients selected from a group consisting of: mullen leaf, witch hazel, baptisia (wild indigo), marshmallow root (*Althea officianales*), *Potentilla tormentilla,* myrrh, agrimony, blood root (sanguinaria), bistort, echinacea, parsley, eucalyptus, wintergreen, rosemary, ginger, sandalwood, sweet almond, sassafrass, linseed oil and castor oil.

The first ten of the ingredients preferably are accessed via herbal tincture media, while the latter ten preferably are accessed in oil forms. Linseed and castor oil preferably are produced by means of cold pressing from their seeds.

The Inventor has discovered that these ingredients act synergistically as dietary supplements to enhance vigorous good health of human beings. When ingested transcutaneously via gums, skin and other cutaneous membranes of humans, these products are useful for reducing plaque and symptoms of gingivitis, gum disorders, cold sores, oral boils, herpes simplex, pimples, acne vulgaris and other disorders susceptible therapeutically to transcutaneous treatment.

When used holistically the ingredients preferably are carried in a treatment medium such as a liquid solution, drops, gumdrops, lozenges, chewing gum, breath dots, toothpaste, a skin patch, an oral rinse, a cream, a poultice, a suppository, an inhaler and/or a douche.

DESCRIPTION OF PREFERRED EMBODIMENTS WITH EXAMPLES

The foregoing and other features and advantages of Applicant's teaching will be understood more fully from discussion of her products and methods of preparation thereof. Modern technology makes it possible to extract more efficiently beneficial substances from leaves, roots and flowers of plants, reducing acrid or toxic aspects thereof. Such technology increases the number of natural ingredients now available from sources once very difficult to isolate.

Mullen leaves, witch hazel, baptisia (wild indigo), marshmallow roots (*althea officianales*), *Potentilla tormentilla,* myrrh, agrimony, blood root (sanguinaria), bistort and eschinacea are all preferably extracted as tinctures in ethyl alcohol.

Parsley, eucalyptus, wintergreen, rosemary, giner, sandalwood, sweet almond and sassafrass are pressed and distilled in oil form. Linseed and castor are cold pressed from their seed.

Applicant selects at least two (2) up to all of the ingredients and combines them in various portions, according to taste and purpose.

Applicant's products are dietary supplements whereby they are eaten and digested.

It will be understood by those familiar with herbs, with their processing and with various percutaneous delivery mechanisms here involved that wide deviations ma be made in the foregoing disclosure without departing from a main theme of invention as set forth in claims which follow. By way of example and not limitation, some of the herbs preferably accessed as tinctures may be accessed as oils and vice versa.

I claim:

1. A food product in liquid form containing at least three herbal ingredients selected from a group consisting of mullen leaf in herbal tincture form, witch hazel in herbal tincture form, baptisia (wild indigo) in herbal tincture form, marshmallow root (*althea Off.*) in herbal tincture form, *Potentilla tormentilla* in herbal tincture form, myrrh in herbal tincture form, agrimony in herbal tincture form, blood root (sanguinaria) in herbal tincture form, bistort in herbal tincture form, eschinacea in herbal tincture form, parsley in oil form, eucalyptus in oil form, wintergreen in oil form, rosemary in oil form, ginger in oil form, sandalwood in oil form, sweet almond in oil form, sassafras in oil form, linseed in oil form and castor in oil form.

2. The food product as claimed in claim 1 with the linseed and castor accessed by cold pressing from their seeds.

* * * * *